United States Patent
Marta et al.

(10) Patent No.: US 10,458,900 B2
(45) Date of Patent: Oct. 29, 2019

(54) GAS DETECTOR WITH NORMALIZED RESPONSE AND IMPROVED SENSITIVITY

(71) Applicant: Honeywell International Inc., Morris Plains, NJ (US)

(72) Inventors: Terry Marta, White Bear Lake, MN (US); James Allen Cox, Monument, CO (US); Bernard Fritz, Eagan, MN (US); Antony Phillips, Poole (GB); Rodney Watts, Wimborne (GB)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 15/759,165

(22) PCT Filed: Sep. 7, 2016

(86) PCT No.: PCT/US2016/050456
§ 371 (c)(1),
(2) Date: Mar. 9, 2018

(87) PCT Pub. No.: WO2017/044436
PCT Pub. Date: Mar. 16, 2017

(65) Prior Publication Data
US 2018/0284012 A1    Oct. 4, 2018

Related U.S. Application Data

(60) Provisional application No. 62/216,929, filed on Sep. 10, 2015.

(51) Int. Cl.
*G01N 21/17*     (2006.01)
*G01N 21/3504*   (2014.01)
(Continued)

(52) U.S. Cl.
CPC ..... *G01N 21/1702* (2013.01); *G01N 21/3504* (2013.01); *G01N 21/37* (2013.01);
(Continued)

(58) Field of Classification Search
CPC ........ G01N 21/1702; G01N 21/3504; G01N 21/37; G01N 29/2425; G01N 29/4427;
(Continued)

(56) References Cited

U.S. PATENT DOCUMENTS 2,424,976 A    8/1947   Golay et al.
2,924,713 A    2/1960   Liston
(Continued)

FOREIGN PATENT DOCUMENTS

AU    582290 B     3/1989
CN    108351293 A  7/2018
(Continued)

OTHER PUBLICATIONS

U.S. Appl. No. 15/767,100, Office Action, dated Aug. 310, 2018, 13 pages.
(Continued)

*Primary Examiner* — Dominic J Bologna
(74) *Attorney, Agent, or Firm* — Wick Phillips Gould & Martin, LLP (57) ABSTRACT

A non-dispersive photoacoustic gas detector includes an infrared light source, a first closed chamber, a first acoustic sensor in fluid communication with the first closed chamber, a second closed chamber, and a second acoustic sensor in fluid communication with the second closed chamber. The first closed chamber comprises a plurality of windows that are substantially transparent to infrared light from the infrared light source. The second closed chamber comprises at least one window that is substantially transparent to infrared light from the infrared light source, and the first closed chamber is arranged in series with the second closed chamber between the infrared light source and the second closed chamber.

19 Claims, 3 Drawing Sheets

(51) Int. Cl.
  *G01N 21/37* (2006.01)
  *G01N 29/24* (2006.01)
  *G01N 29/44* (2006.01)

(52) U.S. Cl.
  CPC ..... *G01N 29/2425* (2013.01); *G01N 29/4427* (2013.01); *G01N 29/4436* (2013.01); *G01N 2021/1704* (2013.01); *G01N 2291/021* (2013.01); *G01N 2291/02809* (2013.01)

(58) Field of Classification Search
  CPC .... G01N 2021/1704; G01M 2291/021; G01M 2291/02809
  See application file for complete search history.

(56) References Cited

U.S. PATENT DOCUMENTS

| | | | |
|---|---|---|---|
| 4,370,553 A * | 1/1983 | Waycaster | G01N 21/03 250/343 |
| 4,436,428 A | 3/1984 | Watanabe et al. | |
| 4,492,862 A | 1/1985 | Grynberg et al. | |
| 4,535,241 A | 8/1985 | Eberhardt | |
| 4,557,603 A | 12/1985 | Oehler et al. | |
| 4,692,622 A | 9/1987 | Taniguchi et al. | |
| 4,736,103 A | 4/1988 | Nelson et al. | |
| 4,738,266 A | 4/1988 | Thatcher | |
| 4,740,086 A | 4/1988 | Oehler et al. | |
| 4,891,629 A | 1/1990 | Gajjar et al. | |
| 4,903,248 A | 2/1990 | Fertig | |
| 5,055,690 A | 10/1991 | Bonne | |
| 5,394,934 A | 5/1995 | Rein et al. | |
| 5,468,961 A | 11/1995 | Gradon et al. | |
| 5,498,873 A | 3/1996 | Liebermann et al. | |
| 5,559,333 A | 9/1996 | Araya et al. | |
| 5,616,826 A | 4/1997 | Pellaux | |
| 5,886,249 A | 3/1999 | Bonne et al. | |
| 5,892,140 A | 4/1999 | Wood | |
| 6,067,840 A | 5/2000 | Chelvayohan et al. | |
| 6,222,190 B1 | 4/2001 | Bernstein et al. | |
| 6,327,896 B1 | 12/2001 | Veronesi et al. | |
| 6,469,303 B1 | 10/2002 | Sun et al. | |
| 6,552,792 B1 | 4/2003 | Pilgrim et al. | |
| 6,628,396 B1 | 9/2003 | Gul | |
| 6,853,449 B2 | 2/2005 | Hocker | |
| 6,878,940 B2 | 4/2005 | Nakamura et al. | |
| 7,034,943 B1 | 4/2006 | Moeckli et al. | |
| 7,045,784 B1 | 5/2006 | Ptasinski et al. | |
| 7,214,939 B1 | 5/2007 | Wong | |
| 7,288,766 B2 | 10/2007 | Uchida et al. | |
| 7,477,993 B2 | 1/2009 | Sunshine et al. | |
| 7,663,756 B2 | 2/2010 | Cole | |
| 7,738,116 B2 | 6/2010 | Kauppinen | |
| 7,797,983 B2 | 9/2010 | Kauppinen | |
| 7,808,640 B2 | 10/2010 | Fritz et al. | |
| 7,895,880 B2 | 3/2011 | Fritz et al. | |
| 7,958,771 B2 | 6/2011 | Rezachek | |
| 7,961,313 B2 | 6/2011 | Van Neste et al. | |
| 8,085,403 B2 | 12/2011 | Fritz et al. | |
| 8,312,758 B2 | 11/2012 | Tobias | |
| 8,322,191 B2 | 12/2012 | Fritz | |
| 8,373,568 B2 | 2/2013 | Moe et al. | |
| 8,451,447 B2 | 5/2013 | Fritz et al. | |
| 8,584,508 B2 | 11/2013 | Rezachek | |
| 8,594,507 B2 | 11/2013 | Youngner et al. | |
| 8,661,874 B2 | 3/2014 | Rezachek | |
| 8,689,607 B2 | 4/2014 | Rezachek et al. | |
| 8,695,402 B2 | 4/2014 | Thorson | |
| 8,701,465 B2 | 4/2014 | Shubinsky et al. | |
| 8,746,038 B2 | 6/2014 | Rezachek | |
| 8,806,916 B2 | 8/2014 | Gautieri | |
| 8,848,191 B2 | 9/2014 | Lust | |
| 8,939,006 B2 | 1/2015 | Rezachek et al. | |
| 9,086,364 B2 | 7/2015 | Rezachek et al. | |
| 9,243,998 B2 | 1/2016 | Avramescu et al. | |
| 9,606,049 B1 | 3/2017 | Yang et al. | |
| 9,829,428 B2 | 11/2017 | Yang et al. | |
| 2004/0036023 A1 | 2/2004 | Hodgkinson | |
| 2006/0138327 A1 | 6/2006 | Kauppinen | |
| 2006/0175547 A1 | 8/2006 | DiFoggio et al. | |
| 2008/0035848 A1 | 2/2008 | Wong | |
| 2008/0277586 A1 | 11/2008 | Cardinale | |
| 2011/0032514 A1 * | 2/2011 | Bitter | G01N 21/37 356/51 |
| 2011/0249262 A1 * | 10/2011 | Russell | G01J 3/02 356/326 |
| 2011/0296900 A1 | 12/2011 | Thorson | |
| 2012/0055232 A1 | 3/2012 | Thornson | |
| 2013/0008229 A1 | 1/2013 | Avramescu et al. | |
| 2013/0086977 A1 | 4/2013 | Wong | |
| 2014/0091014 A1 | 4/2014 | Wagner et al. | |
| 2015/0101395 A1 * | 4/2015 | Dehe | G01N 29/2418 73/24.02 |
| 2017/0102318 A1 | 4/2017 | Yang et al. | |
| 2017/0115207 A1 | 4/2017 | Yang et al. | |
| 2018/0045563 A1 | 2/2018 | Marta et al. | |
| 2018/0299330 A1 | 10/2018 | Yang et al. | |
| 2018/0299369 A1 | 10/2018 | Marta et al. | |

FOREIGN PATENT DOCUMENTS

| | | |
|---|---|---|
| CN | 108369139 A | 8/2018 |
| DE | 2926662 A1 | 1/1981 |
| DE | 3508027 A1 | 9/1986 |
| DE | 19841491 A1 | 9/1999 |
| DE | 102007020596 A1 | 11/2008 |
| DE | 102008018504 A1 | 10/2009 |
| DE | 102012217479 B3 | 10/2013 |
| EP | 1546683 | 8/2004 |
| EP | 2060891 A1 | 5/2009 |
| EP | 2148184 A2 | 1/2010 |
| EP | 2402735 A2 | 1/2012 |
| EP | 2148184 A3 | 12/2012 |
| EP | 3265766 A1 | 1/2018 |
| EP | 3347697 A1 | 7/2018 |
| EP | 3347698 A1 | 7/2018 |
| EP | 3359933 A1 | 8/2018 |
| EP | 3359934 A1 | 8/2018 |
| GB | 710867 | 6/1954 |
| GB | 2358245 A | 7/2001 |
| IN | 288304 | 10/2017 |
| JP | H05172627 A | 7/1993 |
| JP | H05172628 A | 7/1993 |
| JP | 408184501 | 7/1996 |
| JP | H10332579 A | 12/1998 |
| JP | H1172428 A | 3/1999 |
| JP | 2002328116 A | 11/2002 |
| JP | 2007170841 A | 7/2007 |
| JP | 2009257808 A | 11/2009 |
| JP | 2010126465 A | 6/2010 |
| JP | 2010128781 A | 6/2010 |
| JP | 5028080 B2 | 9/2012 |
| SG | 158463 | 2/2010 |
| WO | 9624831 A1 | 8/1996 |
| WO | 9812522 A1 | 3/1998 |
| WO | 2008074442 A1 | 6/2008 |
| WO | 2016141155 A1 | 9/2016 |
| WO | 2017044435 A1 | 3/2017 |
| WO | 2017044436 A1 | 3/2017 |
| WO | 2017062617 A1 | 4/2017 |
| WO | 2017062626 A1 | 4/2017 |

OTHER PUBLICATIONS

PCT Application No. PCT/US2016/050455, International Search Report, dated Dec. 7, 2016, 5 pages.
PCT Application No. PCT/US2016/050455, Written Opinion of the International Searching Authority, dated Dec. 1, 2016, 7 pages.
Dundas M E: "New Technologies in Infrared Hydrocarbon Detection", ISA Transactions, Instrument Society of America, Pittsburgh, U.S., vol. 31, No. 4, 1992, pp. 51-65.
Anonymous: "Flammability limit—Wikipedia, the free encyclopedia", Oct. 21, 2014 (Oct. 21, 2014), Retrieved from the Internet:

(56) References Cited

OTHER PUBLICATIONS

URL: http://web.archive.org/web/20141021101901/http://en.wikipedia.org/wiki/Flammability_limit [retrieved on Nov. 24, 2016] substance table with LEL values; p. 4-p. 8.
PCT Application No. PCT/US20161050456, International Search Report, dated Dec. 12, 2016, 5 pages.
PCT Application No. PCT/US2016/050456, Written Opinion of the International Searching Authority, dated Dec. 12, 2016, 7 pages.
Kari Schjølberg-Henriksen et al., "Sensitive and Selective Photo Acoustic Gas Sensor Suitable for High Volume Manufacturing", IEEE Sensors Journal, vol. 8, No. 9, Sep. 2008, pp. 1539-1545.
PCT Application No. PCT/US2016/050455, International Preliminary Report on Patentability, dated Mar. 22, 2018, 9 pages.
Europe Patent Application No. 16766771.6, Communication Pursuant to Rules 161(1) and 162 EPC, dated Apr. 18, 2018, 3 pages.
PCT Application No. PCT/US2016/050456, International Preliminary Report on Patentability, dated Mar. 13, 2018, 8 pages.
U.S. Appl. No. 15/759,158 entitled "Gas Detector With Normalized Response and Improved Sensitivity", filed Mar. 9, 2018, 49 pages.
Christopher Grinde et al., "A Clover Shaped Silicon Piezoresistive Microphone for Miniaturized Photoacoustic Gas Sensors," Symposium on Design, Test, Integration & Packaging of MEMS/MOEMS, 2009. DTIP MEMS/MOEMS 09, pp. 256-260. Retrieved from the Internet <URL: http://www.eda-publishing.org/dtip09_proceedings.pdf#page=270>.
Kari Schølberg-Henriksen et al., "Sensitive and Selective Photo Acoustic Gas Sensor Suitable for High Volume Manufacturing", IEEE Sensors 2006, EXCO, Daegu, Korea Oct. 22-25, 2006, pp. 679-682.
U.S. Appl. No. 14/879,920, Notice of Allowance, dated Oct. 7, 2016, 10 pages.
International Application No. PCT/US2016/055748, International Search Report, dated Dec. 23, 2016, 4 pages.
International Application No. PCT/US2016/055748, Written Opinion of the International Searching Authority dated Dec. 23, 2016, 7 pages.
International Application No. PCT/US2016/055748, International Preliminary Report on Patentability, dated Apr. 10, 2018, 8 pages.
Yamashita K et al., "Miniaturized infrared sensor using silicon diphragm based on Golay cell", Sensors and Actuators A: Physical, Elesevier BV, NL, vol. 66, No. 1-3, Apr. 1, 1998, pp. 29-32.
Feiertag et al., "Flip Chip MEMS microphone package with large acoustic reference volume", Procedia Engineering, Elsevier, Amsterdam, NL, vol. 5, Jan. 1, 2010, pp. 355-358.
U.S. Appl. No. 15/400,554, Office Action, dated Mar. 3, 2017, 12 pages.
U.S. Appl. No. 15/400,554, Notice of Allowance, dated Oct. 18, 2017, 11 pages.

Europe Patent Application No. 16785292.0, Communication pursuant to Rules 161(1) and 162 EPC, dated May 17, 2018, 3 pages.
U.S. Appl. No. 14/879,920, Corrected Notice of Allowability, dated Feb. 22, 2017, 6 pages.
International Application No. PCT/US2016/055759, International Search Report dated Jan. 23, 2017, 4 pages.
International Application No. PCT/US2016/055759, Written Opinion of the International Searching Authority dated Jan. 23, 2017, 7 pages.
David Klocke et al: "Infrared receptors in pyrophilous ("fire loving") insects as model for new un-cooled infrared sensors". Beilstein Journal of Nanotechnology, vol. 2, Mar. 30, 2011, pp. 186-197.
International Application No. PCT/US2016/055759, International Preliminary Report on Patentability dated Apr. 10, 2018, 8 pages.
Europe Patent Application No. 16784357.2, Communication pursuant to Rules 161(1) and 162 EPC, dated Jun. 7, 2018, 3 pages.
U.S. Appl. No. 15/767,100 entitled "Electromagnetic Radiation Detector Using a Planar Golay Cell", filed Apr. 9, 2018, 21 pages.
PCT Application No. PCT/US2016/020637, International Search Report, dated Jun. 15, 2016, 3 pages.
PCT Application No. PCT/US2016/020637, Written Opinion of the International Searching Authority, dated Jun. 15, 2016, 6 pages.
PCT Application No. PCT/US2016/020637, International Preliminary Report on Patentability, dated Sep. 5, 2017, 7 pages.
Europe Patent Application No. 16710887.7, Communication pursuant to Rules 161(1) and 162 EPC, dated Oct. 12, 2017, 2 pages.
Europe Patent Application No. 16766770.8, Communication pursuant to Rules 161(1) and 162 EPC, dated Apr. 18, 2017, 3 pages.
U.S. Appl. No. 15/767,100, Office Action, dated Aug. 31, 2018, 13 pages.
U.S. Appl. No. 15/767,100, Final Office Action, dated Dec. 18, 2018, 7 pages.
U.S. Appl. No. 15/767,100, Advisory Action, dated Mar. 1, 2019, 3 pages.
U.S. Appl. No. 15/555,762, Office Action, dated Dec. 31, 2018, 9 pages.
Europe Patent Application No. 16785292.0, Extended European Search Report, dated Mar. 13, 2019, 12 pages.
U.S. Appl. No. 15/767,100, Notice of Allowance, dated Apr. 3, 2019, 8 pages.
PCT Application No. PCT/US2016/050455, Written Opinion of the International Searching Authority, dated Dec. 7, 2016, 7 pages.
PCT Application No. PCT/US2016/050456, International Search Report, dated Dec. 12, 2016, 5 pages.
Kari Schjølberg-Henriksen et al., "Sensitive and Selective Photo Acoustic Gas Sensor Suitable for High Volume Manufacturing", IEEE Sensors 2006, EXCO, Daegu, Korea Oct. 22-25, 2006, pp. 679-682.

* cited by examiner

GAS DETECTOR WITH NORMALIZED RESPONSE AND IMPROVED SENSITIVITY

CROSS-REFERENCE TO RELATED APPLICATIONS

The present application claims priority to and is the National Stage of International Application No, PCT/US2016/050456, filed on Sep. 7, 2016 and entitled "Gas Detector with Normalized Response and Improved Sensitivity," which claims priority to U.S. Provisional Patent Application Ser. No. 62/216,929, filed on Sep. 10, 2015 and entitled "Gas Detector with Normalized Response and Improved Sensitivity," both of which are incorporated herein by reference in their entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Photoacoustic measurement is based on the tendency of molecules in a gas, when exposed to certain wavelengths of radiant energy (e.g. infrared light), to absorb the energy and reach higher levels of molecular vibration and rotation, thereby reaching a higher temperature and pressure within a measurement cell. When the radiant energy striking a gas is amplitude modulated at a known frequency, the resulting fluctuations in energy available for absorption produce corresponding temperature and pressure fluctuations in the gas, which can be measured as an acoustic signal. The amplitude of the acoustic signal is proportional to the intensity of the radiation and the concentration value of the absorbing gas. Such devices can be used to measure small concentration values of gases in a sample.

SUMMARY

In an embodiment, a non-dispersive photoacoustic gas detector comprises an infrared light source, a closed chamber, and an acoustic sensor in fluid communication with the closed chamber. The closed chamber comprises at least one window that is substantially transparent to infrared light from the infrared light source, and the closed chamber is spaced apart from the infrared light source. The closed chamber is substantially sealed.

In an embodiment, a non-dispersive photoacoustic gas detector comprises an infrared light source, a closed chamber, a gas sample disposed within the closed chamber, and an acoustic sensor in fluid communication with the closed chamber. The closed chamber comprises at least one window that is substantially transparent to infrared light from the infrared light source, and the gas sample can comprise a gas or a mixture of at least two gases.

In an embodiment, a method of detecting a gas comprises passing infrared light through a light path, where the light path comprises one or more target gases, absorbing, by the one or more target gases, at least a portion of the infrared light in the light path, passing the infrared light into a closed chamber that contains a gas sample after passing the infrared light through the light path, generating an acoustic signal within the closed chamber in response to passing the infrared light into the closed chamber, detecting the acoustic signal, and converting the acoustic signal into a response. The closed chamber comprises at least one window that is substantially transparent to the infrared light, and the acoustic signal decreases in response to an increased concentration of the one or more target gases in the light path.

In an embodiment, a non-dispersive photoacoustic gas detector comprises an infrared light source, a first closed chamber having a plurality of windows that are substantially transparent to infrared light from the infrared light source, a second closed chamber having at least one window that is substantially transparent to infrared light from the infrared light source, a first acoustic sensor in fluid communication with the first closed chamber, and a second acoustic sensor in fluid communication with the second closed chamber. The first closed chamber is arranged in series with the second closed chamber between the infrared light source and the second closed chamber.

In an embodiment, a non-dispersive photoacoustic gas detector comprises an infrared light source, a plurality of closed chambers arranged in series with respect to a light path from the infrared light source, and a plurality of acoustic sensors. Each acoustic sensor of the plurality of acoustic sensors is associated with a corresponding closed chamber of the plurality of closed chambers, and each acoustic sensor is in fluid communication with the corresponding closed chamber. A first closed chamber of the plurality of closed chambers comprises a first sample gas, and a second closed chamber of the plurality of closed chambers comprises a second sample gas. The second sample gas has a different composition than the first sample gas, and the plurality of closed chambers comprises a transparent pathway through the plurality of closed chambers.

In an embodiment, a method of detecting a gas comprises passing infrared light through a light path that comprises one or more target gases, absorbing, by the one or more target gases, at least a portion of the infrared light in the light path, passing the infrared light into a first closed chamber after passing the infrared light through the light path, generating a first acoustic signal within the first closed chamber in response to passing the infrared light into the first closed chamber, passing the infrared light through the first closed chamber into a second closed chamber, generating a second acoustic signal within the second closed chamber in response to passing the infrared light into the second closed chamber, detecting the first acoustic signal and the second acoustic signal, and converting the first acoustic signal and the second acoustic signal into a response. The first closed chamber comprises a plurality of windows that are substantially transparent to the infrared light, and the first closed chamber comprises a first gas sample. The second closed chamber comprises at least one window that is substantially transparent to the infrared light.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Disclosed herein are improved photoacoustic sensors and methods of detecting one or more gases. The photoacoustic effect has been used to irradiate a gas sample to produce an acoustic response based on the absorption of a portion of the radiation to produce heat and a corresponding pressure response. At low gas concentrations, the acoustic response can be minimal, which may require a sensitive acoustic sensor to detect the acoustic signal. When the sensors are used in certain environments, noise from the environment can mask the actual acoustic response. For example, an industrial setting may include various mechanical equipment that can create noise issues. While the noise may not occur at the same frequency as the modulated light, and therefore the acoustic response, the magnitude of the noise may be sufficient to create an unacceptably low signal to noise ratio, which may make detection of the presence of the gas difficult.

The present system does not rely on an acoustic response from a target gas in the environment. Rather, a closed chamber or cell is used to retain a gas sample. Radiation incident upon the closed chamber may produce an acoustic response that can be detected by an acoustic sensor. The concentration of the gas sample can be carefully controlled within the closed and sealed chamber, thereby producing an acoustic response having a relatively large acoustic magnitude. When no gases that absorb radiation in the same wavelength ranges are present between a source of the radiation and the closed chamber, the acoustic response may be at or near peak. When a target gas having an absorption profile similar to the gas in the closed chamber is present between the source of the radiation and the closed chamber, a portion of the radiation will be absorbed prior to the radiation reaching the closed chamber. The target gas then acts as a filter for the radiation, which results in a decreased acoustic response for the gas in the closed chamber. The decreased acoustic response can be detected by the acoustic sensor and converted into a gas concentration in the light path between the source of the radiation and the closed chamber.

This process can be used to determine a number of responses including a concentration of one or more components present in the light path. It has also been discovered that when a gas or gas mixture is selected for use in the closed chamber, an overall or normalized response to a plurality of gases can be detected. The normalized response may include a measurement of a gas that is not present in the closed chamber. For example, a mixture of methane and ethane can be used to detect the presence of not only methane and ethane, but also of a wide range of hydrocarbons. The normalized response may be useful in determining overall measurements such as levels relative to flammability limits, toxicity exposures, calorific value, and the like.

The photoacoustic sensor disclosed herein can also include a plurality of closed chambers arranged in series where the radiation passes through a first closed chamber, then through a second closed chamber, etc. The ability to have multiple closed chambers in series can allow for individual target gas concentrations to be determined based on the acoustic response in different closed chambers. Multiple normalized responses or a normalized response in addition to one or more gas concentrations can also be determined.

In some embodiments, one or more of the plurality of cells can be used with a reference gas. The reference gas may absorb over a different wavelength range than the other sample gases, and may also have different absorption characteristics than a gas present in the light path. The reference gas can then be used to provide an indication of environmental effects on the acoustic response in the other closed chambers. For example, the reference signal can be used to determine any drop in the intensity of the radiation output, any loss of intensity due to fouling of the detector (e.g., a fogged or dirty window, etc.), or any substances in the light path that may affect the intensity of the radiation (e.g., dust, water vapor, etc.). The reference chamber can also be used to ensure that radiation is being received. If the reference chamber does not produce an acoustic response, then an indication that the radiation is not present may be generated. This may help ensure that the system is operating. In comparison, a zero response in a prior system may simply be interpreted as a lack of the presence of a target gas when in fact the light source is not working. Thus, the system disclosed herein may provide several advantages and improvements in the field of gas detection.

Figure 1:
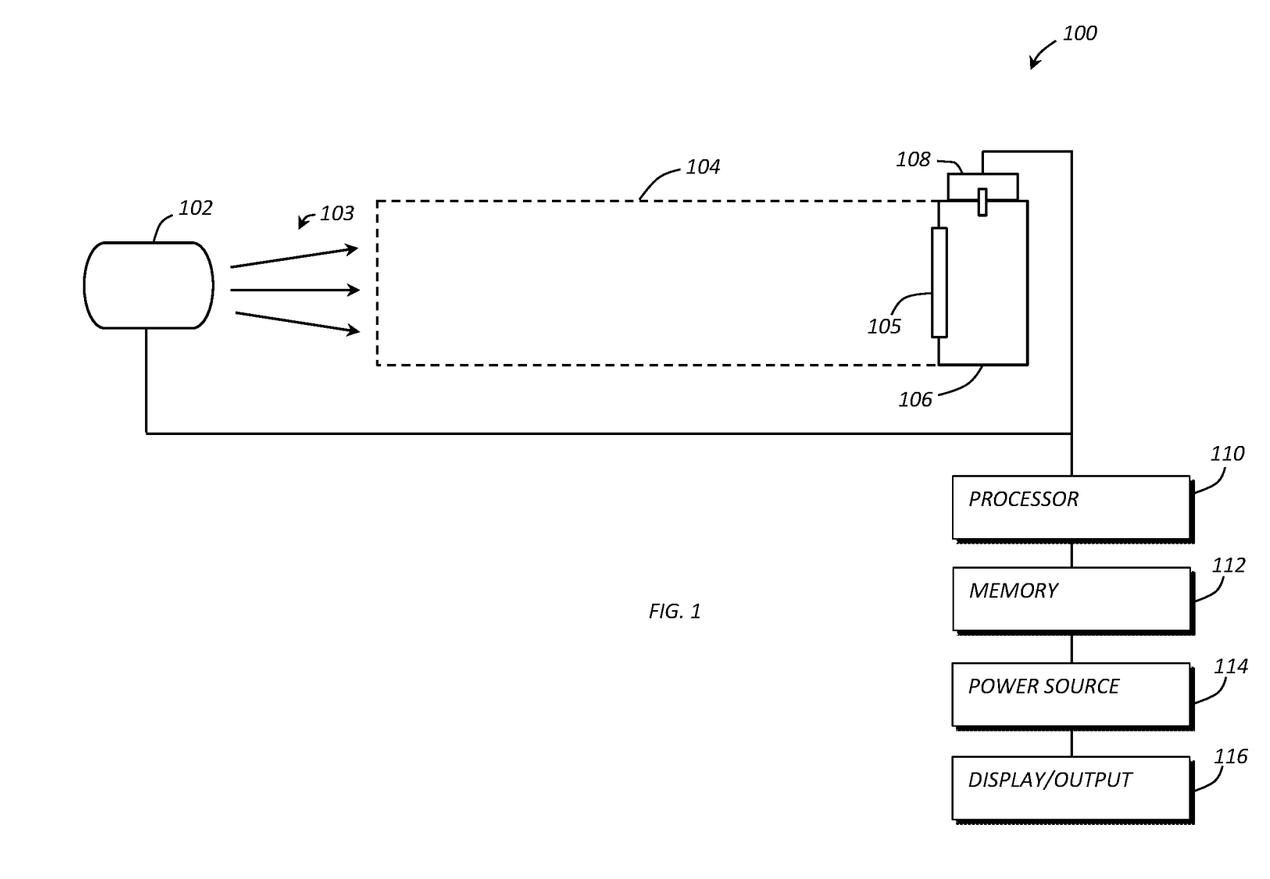
FIG. 1 schematically illustrates a photoacoustic sensor according to an embodiment.

FIG. 1 schematically illustrates an embodiment of a photoacoustic sensor 100. The photoacoustic sensor 100 comprises a light source 102 producing radiation 103, a light path 104, a closed chamber 106, and an acoustic sensor 108 in fluid and/or pressure communication with the interior of the closed chamber 106. A window 105 can be used to allow light to pass into the closed chamber 106. The photoacoustic sensor 100 can also include, in some embodiments, a control system including a processor 110, a memory 112, a power source 114, and a display/output device 116 that can be used to control the various elements of the system and/or process the outputs (e.g., an acoustic signal generated by the acoustic sensor 108.

The light source 102 serves to provide a source of modulated light through the light path 104 and into the closed chamber 106. The efficiency at which a gas absorbs radiant energy can vary with the radiation frequency of the energy. Energy absorption by a particular gas over a frequency spectrum typically includes narrow bands or lines of high absorptivity, spaced apart from one another by frequency bands of much lower absorptivity. Each gas has a unique absorptivity spectrum, which may be referred to as an absorption profile. Accordingly, the light source 102 can be selected to produce a frequency band or range encompassing the absorption profile or lines of the gas of interest. In some embodiments, a plurality of gases of interest can be radiated at the same time, and the resulting frequency band of the light can be selected to provide a suitable amount of radiation 103 at the desired frequency to produce a measureable output signal across the plurality of gases.

In an embodiment, the light source 102 can emit narrow or broadband electromagnetic radiation in the infrared region. In an embodiment, the light source 102 can include an incandescent lamp, a black-body radiation source, or another emitter of electromagnetic radiation in the infrared spectrum. In some embodiments, the light source 102 can be a light emitting diode (LED), an array of LEDs, a laser, a laser diode, or the like. In an embodiment, the light source 102 can produce a broadband radiation in the infrared range. In some embodiments, an optional filter can be used with the light source 102 or the closed chamber 106 to select a specific wavelength range from the radiation 103 produced by the light source 102, as described in more detail herein.

The radiation 103 from the light source 102 can be modulated to provide the acoustic response in the closed chamber 106. Various types of modulators can be used. In an embodiment, the light source 102 can be modulated and/or the radiation 103 can be mechanically or electrically modulated after being produced by the light source 102. For example, a controller can control the power signal to the light source 102 to produce a modulated radiation output. The radiation 103 can also be modulated after being produced by the light source 102, including the use of modulation mechanisms such as mechanical choppers (e.g., a rotating disc with passages therethrough, a rotating mirror, etc.), interference gratings or filters, interferometers, or the like. In some embodiments, optical modulators can also be used to modulate the radiation 103 from the light source 102 including, but not limited to, acousto-optic modulation, electro-optic modulation, magneto-optic modulation, and the like.

The radiation 103 can be modulated at a frequency that allows the acoustic signal to be detected, and the detection limits of the acoustic sensor along with any background noise can be taken into consideration when selecting the modulation rate. The radiation 103 can be modulated at a frequency of at least about 1 Hz, or at least about 10 Hz, though in some embodiments, the radiation 103 can be modulated at a lower frequency. In some embodiments, the radiation 103 may be modulated at higher frequencies in order to decrease the sensitivity of the photoacoustic sensor 100 to acoustical background noise. In an embodiment, the radiation 103 may be modulated at a frequency between 10 Hz and 100 kHz.

The radiation 103 produced by the light source 102 may travel to the closed chamber 106 through a light path 104. As the radiation 103 travels through the light path 104, any gases present that absorb radiation at a frequency present in the radiation may absorb a portion of the radiation 103 and act as a filter for the radiation 103 reaching the closed chamber 106. The amount of radiation 103 absorbed may depend on the amount of the gas present in the light path 104, the length of the light path 104, the type of gas, the frequency range of the radiation present, and the absorption characteristics of the gas.

In some embodiments, the light path 104 may be an open pathway that is not enclosed. This embodiment may be useful for the detection of components present in atmospheric gases and/or within the interior of vessels or other enclosures where the components may normally be found. For example, a light source 102 can be placed separate from the closed chamber 106 with only atmospheric gases present between the light source 102 and the closed chamber 106.

In some embodiments, the light path 104 may comprise a waveguide to allow the radiation 103 to pass from the light source 102 to the closed chamber 106. The waveguide can comprise an optional enclosure or chamber. The enclosure can include a closed pipe, conduit, or other vessel. The interior of the enclosure can be polished to retain the radiation 103 within the enclosure and guide the radiation 103 to the closed chamber 106. The enclosure can have any suitable cross-sectional shape and can be formed of a material suitable for use with the gases of interest. In some embodiments, the enclosure can be formed from a metal (e.g., stainless steel, copper, aluminum, etc.), a polymeric material, a ceramic or glass, or the like. The enclosure may have a length selected to allow a sufficient amount of absorption by a target gas. When very low concentrations are expected, the light path 104 may be longer than when moderate to high concentrations are expected. In an embodiment, the light path 104 may have a length between about 5 mm and about 10 m. For example, path lengths for point measurements may be between about 10 cm and about 50 cm. Path lengths for use in ducts can be less than about 0.5 m for small ducts, between about 0.5 m and about 1 m for medium ducts, and between about 1 m and about 10 m for larger ducts. In some embodiments, path lengths longer than 10 m (e.g., up to about 100 m) may be possible when wave guides are used to focus the radiation and/or focused beams of radiation are used across such distances.

In some embodiments, the waveguide can comprise a portion used to guide the radiation 103 from the light source 102. For example, a glass or other solid portion (e.g., optical elements such as lenses, reflectors, focusing elements, and the like) can be used to guide the radiation into alignment with an ambient gas.

The use of an enclosure or chamber may allow the gases within the enclosure to be isolated from the atmosphere, which may be useful for toxic gases or other substances confined to enclosed spaces. Fluid conduits can be coupled to the enclosure to provide fluid communication between the interior of the enclosure and another source of the gas being measured. For example, the enclosure may be in fluid communication with a gas pipeline, a tank interior, a closed system loop, or the like to allow for the detection of one or more components without the need for the gases to be exposed to the environment or for the light source 102 or closed chamber 106 to be placed within the system.

In still other embodiments, the light path 104 may include the optional enclosure and be in fluid communication with the gases present adjacent to the photoacoustic sensor 100. In this embodiment, an opening, aperture, porous membrane, or other permeable opening may be associated with the enclosure to allow the gases adjacent the enclosure to enter into the light path 104 between the light source 102 and the closed chamber 106.

The closed chamber 106 serves to retain a sample of a gas or gas mixture of interest and allow the sample to be irradiated by the radiation 103 that passes through the light path 104. In an embodiment, the closed chamber 106 can comprise a window 105 that allows the radiation 103 to pass into the interior of the closed chamber 106. The closed chamber 106, along with the acoustic sensor 108, may be substantially sealed so that the sample of gas remains within the closed chamber 106 and is not exchanged with any external gasses or fluids.

The closed chamber 106 comprises a wall structure that can include a generally rectilinear shape such as a cube, or alternatively, a cylinder, or any other suitable shape. The dimensions of the closed chamber 106 can vary and may be selected to provide a predetermined volume or size. In an embodiment, the closed chamber 106 can have dimensions (e.g., length, width, diameter, and/or height) between about 1 mm and about 50 mm, though one or more of the dimensions can be larger than 50 mm in some instances. The closed chamber 106 may define a closed interior space having a volume of between about 0.001 $in^3$ to about 1 $in^3$, or between about 0.005 $in^3$ to about 0.5 $in^3$, though larger or smaller interior volumes may also be suitable.

The closed chamber 106 can be constructed of various materials that are suitable for containing the sample within the interior of the closed chamber 106. In an embodiment, the outer wall may comprise a metal, such as aluminum, stainless steel, copper, brass, or the like. In some embodiments, the outer wall may comprise a plastic, or polymer, such as methacrylate. The outer walls can also be formed of a ceramic or glass. The wall thickness can be selected to provide a suitable structural support and pressure containment. In some embodiments, the walls of the closed chamber 106 can be constructed of a transparent material including polymers, ceramics, glass, or the like, where the material may be transparent to at least infrared radiation. This may reduce any heating effects associated with the walls when radiation is incident upon the walls.

In some embodiments, at least a portion of the wall or interior surface of the closed chamber 106 can be mirrored. The mirrored finish can serve to reflect light back into the interior of the closed chamber 106 to provide an increased absorption and acoustic response from the gas or mixture of gases in the closed chamber 106. The mirrored finish can be on any portion of the closed chamber 106. For example, a mirror finish (e.g., an evaporated metal layer, etc.) can be formed on an external surface of the wall of the closed chamber 106 where the wall is constructed of a transparent material. In some embodiments, an internal metal surface can be polished to produce a mirrored finish. In still other embodiments, a mirror finish can be formed on one or more portions of the interior surface of the closed chamber 106.

In an embodiment, a rear portion of the closed chamber 106 can comprise a mirrored surface. The mirrored surface may be configured to direct the radiation 103 from the light source 102 back through the closed chamber 106 to the light source 102 and/or a position near the light source 102. A corresponding mirror can be placed at the light source 102 and/or near the light source 102 to then reflect the radiation 103 back through the light path 104 to the closed chamber 106. This arrangement may be useful in increasing the effective path length along which the radiation 103 passes, which can be used to improve the detection limits of the photoacoustic sensor 100 for small concentrations of the gas(es) of interest.

In some embodiments, the walls can be formed, at least partially, of a transparent material such as a glass or a polymer that is transparent to infrared radiation in the wavelength of interest while being impermeable to fluids (e.g., impermeable to gasses and liquids). In some embodiments, at least a portion of a wall section can be provided with a narrowed portion to allow the portion of the wall to serve as the window 105 and improve transmission of the radiant energy into the interior of the closed chamber 106.

A closed chamber 106 that is constructed of a transparent material such as a polymeric material may provide several advantages. First, the material of the closed chamber 106 can react to the radiation 103 in the same manner as the gas and cause localized warming in response to the radiation. A transparent material may allow the radiation 103 to pass through the walls rather than being converted into heat. In addition, the transparent materials may have a greater compliance and have a reduced transmittance of any ambient sound signals better than metals. This may serve to shield signal noise from interfering with the acoustic signal generated within the gas sample.

The window 105 comprises an opening through a wall section to allow the radiation 103 to pass into the interior of the closed chamber 106. In an embodiment, the window 105 can comprise an insert into an opening formed in the wall of the closed chamber. The window 105 can be sealingly engaged with the opening in order to prevent the escape of the sample or the entry of any external gases into the closed chamber 106. The window 105 can be formed from various materials so long as the material is at least partially transparent to infrared radiation. In an embodiment, the window 105 can comprise a glass. Other suitable materials can include fused quartz (e.g., a UV fused quartz), germanium, sapphire, silicon, or the like.

In an embodiment, the window 105 can have a shape designed to direct the radiation 103 into the closed chamber 106. Since the window 105 is transparent, the window 105 can form a lens to direct the radiation 103 into the closed chamber 106. The window 105 can comprise a converging lens configured to direct the radiation 103 passing through the light path 104 into the closed chamber 106. The power of the lens can be selected depending on the desired focus point within the closed chamber 106 or past the closed chamber 106. In some embodiments, two or more windows 105 can be used to shape and/or direct the radiation 103 into a desired beam.

The window material and/or thickness can be selected to have some filtering properties for the radiation. While an optional filter element can also be used, the window may be selected to provide a desired degree of filtering without the need for an additional filter. For example, the window material may be selected to filter infrared wavelengths in the region absorbed by water and/or carbon dioxide, both of which can cause interference with the resulting acoustic signal. As a specific example, a window material comprising fused UV quartz may serve as a filter for blocking transmission of infrared waves in the range of 2.6 µm to 2.9 µm, which corresponds to the approximate absorption wavelengths of water and carbon dioxide. The amount of filtering can be based on the thickness of the window, and both the selection of the window material and the thickness can determine the amount of filtering provided by the window (e.g., the amount of absorption of wavelengths corresponding to water and carbon dioxide). As a result, the window material may serve as a filter without the need for any additional, optional filters.

An optional filter can be provided in the light path 104 to select a desired portion of the radiation spectrum to pass into the closed chamber 106. The filter can be placed adjacent to the light source 102 and/or adjacent to the closed chamber 106, or at any point in between the light source 102 and the closed chamber 106. In an embodiment, the filter can be placed adjacent to the window 105, and in some embodiments, may be coupled to or deposited on a surface of the window 105.

The optional filter can be made of a material that is selectively transparent to infrared radiation in a desired wavelength range. The selectively can be chosen based on the absorption profile of a particular target gas or gasses. For example, a filter may transmit the radiant energy only within a somewhat narrowed waveband or frequency bandwidth. The transmission frequency through the filter can be chosen to broadly coincide with the strongest absorption bands of each gas to be detected.

The acoustic sensor 108 is in fluid communication with the interior of the closed chamber 106 and serves to detect pressure changes resulting in an acoustic signal originating within the closed chamber 106. The pressure changes within the closed chamber 106 are caused by gases absorbing the radiant energy of specific wavelengths of the radiation 103 and changing temperature as a result. The resulting temperature fluctuations in the gas correspond to the modulation frequency of the radiation 103 from the light source 102. The temperature changes result in pressure changes within the closed chamber 106 that can be detected with the acoustic sensor 108. Any suitable acoustic sensor or transducer can be used. In some embodiments, the acoustic sensor 108 can include a microphone, a pressure transducer (e.g., a piezoelectric transducer, an electrostatic transducer, a flow based transducer, an optical transducer, an electrically sensitive element, etc.). The acoustic sensor 108 may be capable of detecting an acoustic signal in the frequency range corresponding to the modulation frequency of the radiation from the light source 102. In an embodiment, the acoustic sensor can comprise a microphone. In some embodiments, the acoustic sensor may comprise a piezoelectric material.

The acoustic sensor 108 can be positioned to detect the pressure changes within the closed chamber 106. In some embodiments, the acoustic sensor 108 can be in a separate component from the closed chamber 106 and can be fluidly coupled to the closed chamber 106 by an aperture or other opening. The combination of the acoustic sensor 108, the aperture, and the interior of the closed chamber 106 may form a closed chamber or cell that is substantially sealed. In some embodiments, a flexible, impermeable membrane can be disposed between the interior of the closed chamber 106 and the acoustic sensor 108 to allow for the transmission of the pressure signal between the closed chamber 106 and the acoustic sensor 108 while preventing the sample gas or gasses from directly contacting the acoustic sensor 108.

While shown in FIG. 1 as having the acoustic sensor 108 in a separate chamber, the acoustic sensor 108 can be placed directly within the closed chamber 106 and/or form a portion of a wall of the closed chamber 106. Signal lines can be used to provide a connection between the acoustic sensor 108 and the processor 110, memory 112, and power source 114.

In some embodiments, a plurality of acoustic sensors can be associated with the photoacoustic sensor 100. For example, a plurality of acoustic sensors 108 can be positioned to detect pressure changes within the closed chamber 106. The use of multiple acoustic sensors may provide redundancy in the event of an acoustic sensor failure, error reduction through the use of combined signal analysis, and/or noise cancellation across the cell. In some embodiments, an additional acoustic sensor 108 can be associated with the photoacoustic sensor 100 in order to detect ambient and/or background noise. The ambient noise detector can be sealed from the closed chamber 106 to detect ambient signals rather than a signal generated within the closed cell 106. The resulting ambient and/or background signal can be used to correct the output signal from the acoustic sensor 108 detecting a signal from the photoacoustic sensor 100 to account for noise, etc.

In some embodiments, additional and optional sensors can be used with the system to provide environmental data that can be used in correcting a detected signal. In some embodiments, the photoacoustic sensor 100 can be used to determine a concentration value of a target component in the light path 104. The term "concentration value" is used herein to denote a measured signal corresponding to the number of gas molecules in the light path 104. The concentration value may depend on the gas concentration in the light path 104, which can vary with changes in ambient temperature and ambient pressure. For example, the approximate elevation of the photoacoustic sensor 100 affects the pressure of the target gases in the light path when the light path contains atmospheric gases. In order to correct the concentration values for temperature and pressure variations, a temperature and/or pressure sensor may also be present. The temperature and/or pressure sensors may be in signal communication with the processor 110 and the resulting measured value or values can be used to correct the calculated concentration value. Any suitable temperature sensor (e.g., a thermocouple, etc.) and/or pressure sensor can be used with the system.

In some embodiments, a light sensor such as a photodiode can be used to ensure that the light source 102 is generating radiation. The photodiode can be placed behind the light source 102 (e.g., in a position with light incident upon the photodiode), within the light path 104, within the closed chamber 106, and/or behind the closed chamber 106 to provide an indication of the presence of the radiation 103, and in some embodiments, an intensity of the radiation 103. The light sensor may provide a safety check to ensure that the radiation 103 is present, and may also be used to correct the output values from the acoustic sensor 108 based on the detected intensity.

A processor 110 can receive and convert the signals from the acoustic sensor 108 into a response such as a concentration value of a component within the light path 104. The processor 110 can be in signal communication through a wired and/or wireless connection with the light source 102 along with the acoustic sensor 108. The processor 110 can include circuitry for controlling the modulation of the light source 102, as well as circuitry for receiving and processing signals from the acoustic sensor 108, and optionally, a temperature sensor, a pressure sensor, and/or one or more photodiodes.

In an embodiment, the processor 110 may comprise a microcontroller. As used herein, the term "processor" can refer to any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), or any other type of processor or processing circuit.

The memory 112 is used by the processor circuitry during operation, and may include random access memory (RAM), one or more hard drives, and/or one or more drives that handle removable media. The memory 112 can include a non-transitory memory for retaining a control and/or processing program that can execute upon the processor 110.

The output or display device 116 can be used to indicate the presence and respective concentration values of the particular gases within the light path 104. The display device 116 may comprise any suitable output device, including a video terminal, LED indicator, analog gauge, printer, or other peripheral device. Generally, the display device 116 may indicate concentration measurements of a particular gas in terms of parts per million (ppm) and/or partial pressure. The display devices 116 may also be used to indicate the modulation frequency of the radiation 103. In some embodiments, the display device 116 can be used to present alarms or other warning conditions if a concentration value or level is above a threshold.

The power source 114 can provide power to the light source 102, acoustic sensor 108, temperature sensor, pressure sensor, photodiode, processor 110, memory 112, and display device 116. In an embodiment, the power source 114 may comprise a battery, such as a rechargeable lithium-ion battery. In an alternative embodiment, power source 116 may comprise an alternating current (AC) adaptor.

The processor 110 can transform the signal using various algorithms to identify the one or more gases within the light path 104 and a concentration corresponding to each of those gases. Specifically, the processor 110 may contain a file providing a base acoustic response measurement when no gas is present in the light path 104. The base acoustic response may be considered an upper response level. When a gas is present in the light path 104, the gas may absorb along one or more lines in the frequency range available in the radiation spectrum. The absorption may filter the radiation signal reaching the closed chamber 106. A decrease in the output signal of the sample gas within the chamber may result from the absorption of the gas in the light path 104. The degree of the decrease in the signal output within the closed chamber 106 can be correlated to the concentration of the target gas present in the light path, and the processor 110 may utilize a correlation, optionally along with the ambient pressure and temperature and/or the radiation intensity, to determine a concentration value of the target gas in the light path 104.

Thus, the present system relies upon a decrease in the output signal to determine an increase in the presence of a target gas in the light path. The concentration determination may be advantageous by providing a high signal to noise ratio at low concentration values. In contrast to systems relying on an acoustic response at low concentrations, the noise level from various sources including ambient acoustic signals may not significantly interfere with the concentration determination. Further, the length of the light path 104 can be configured to provide a desired level of sensitivity wherein a long light path may provide a greater sensitivity to lower concentration values.

The photoacoustic sensor 100 can be used to detect a gas in an environment. The detection process can begin with the light source 102 producing a radiation 103 that can be modulated and passing the radiation 103 through a light path 104. The light path 104 can comprise one or more target gases whose concentration is being measured. The one or more target gases can absorb at least a portion of the radiation 103. For example, the target gas in the light path 104 can absorb radiation 103 at certain frequencies. The remaining radiation 103 having the portion of the energy absorbed can pass to the closed chamber 106 through the window 105.

The interaction of the remaining radiation 103 with the sample gas in the closed chamber 106 can cause temperature changes, and corresponding pressure changes, within the closed chamber 106 that correspond to the modulation frequency of the radiation 103. The pressure changes results in an acoustic signal being generated within the closed chamber 106, and the acoustic signal can be detected with the acoustic sensor 108. The acoustic signal can be converted into a response upon being sent to the processor 110. In an embodiment, the response can comprise a concentration value of the target gas in the light path 104. For example, the processor 110 may then be used to perform calculations on the electrical signal produced by the acoustic sensor 108, which allows for the determination of the presence and concentration of one or more gases in the light path 104. In some embodiments, various additional inputs can be used in the determination of the concentration value including a temperature input, an ambient pressure input, an intensity measurement of the radiation 103, or the like.

In an embodiment, a single sample gas may be present in the closed chamber 106 alone or in combination with a carrier gas. The optional carrier gas may not absorb at the same frequency as the sample gas or may not substantially absorb infrared radiation. As a result, the carrier gas may not contribute to the acoustic response within the closed chamber 106. The use of the carrier gas may allow the concentration of the sample gas within the closed chamber 106 to be controlled to produce a desired acoustic response based on an input radiation intensity. The carrier gas can also be used to control the pressure within the closed chamber 106, which may be useful for controlling leaks and the partial pressure of the sample gas or gasses present in the closed chamber 106.

The use of a single sample gas may allow the presence of the same gas to be detected in the light path 104. For example, the use of methane in the closed chamber 106 may be used to detect the presence of methane in the light path 104 based on a decrease in the detected acoustic signal generated within the closed chamber 106. In this embodiment, the gas sample within the closed chamber may allow for a concentration value of the same gas in the light path 104 to be determined.

In some embodiments, a single gas or a mixture of sample gases can be present in the closed chamber 106, which can be used to produce a normalized response to a mixture of gases in the light path 104. In general, various gases may have similar absorption characteristics based on a similarity of internal bonds and structures. For example, a mixture of light hydrocarbons such as methane, ethane, propane, and butane, may exhibit some overlapping absorption characteristics when present in a mixture. A mixture of a plurality of sample gases that are selected to have absorption ranges that overlap with the gases that can be present in the light path can be used to provide an overall indicator of the presence of the gas.

As used herein a "normalized response" refers to an indication of a level of the gas in the light path without providing a direct indication of the individual concentration of each gas in the light path. The normalized response may also contain an indication of the presence of a gas that is not present in the sample in the closed chamber 106. This type of response may be useful in several areas including determining a presence of one or more gases relative to an explosion limit, an exposure threshold, a toxicity threshold, or any combination thereof. The explosion limit, which can also be referred to as a flammability limit, refers to the range of concentrations of a flammable mixture in air that will combust. The explosion limit has both an upper concentration limit (e.g., an upper explosion limit) and a lower concentration limit (e.g., a lower explosion limit or LEL). Outside of this concentration range, the flammable mixture will not combust in the air. The LEL can be monitored to prevent a concentration of flammable gases from accumulating and potentially leading to an explosive condition. The exact threshold for the LEL varies from jurisdiction to jurisdiction, but the LEL thresholds generally represent a fraction of the LEL that is allowable before an alarm should be triggered.

In an embodiment, the photoacoustic sensor 100 can be used to produce a normalized response that is indicative of the LEL of various flammable mixtures. Different sample gases can be selected to produce the acoustic response in the closed chamber 106 to indicate an overall concentration of flammable components in the light path 104, without being specific to one or more flammable components. The choice of the gas or mixture of gases can be based on the ability of the gas or mixture of gases to remain a gas over the operating temperature range (e.g., having a boiling point below about −40° C., etc.), the absorption of wavelengths of radiation in a range that overlaps with the gases of interest (e.g., absorbs radiation in the wavelengths from about 3.2 µm to about 3.6 µm), the ability of the gas or mixture of gases to avoid absorption in a range corresponding to potential interfering compounds (e.g., avoids $CO_2$ absorption between about 4.2 µm and about 4.35 µm), and/or the relative toxicity of the gas or mixture of gases to provide for safe handling and use of the device. In some embodiments, the selection and/or concentration of the gas or mixture of gases can be based on the desired sensitivity and geometry of the gas detector and the length of the light path 104.

In some embodiments, the concentration of flammable components in the light path can be correlated to an LEL using a mixture of gases in the sample chamber comprising methane, ethylene, ethane, propane, difluoromethane, chlorofluoromethane, chlorodifluoromethane, trifluoromethane, propene, propylene, tetrafluoroethylene, pentafluoroethane, trifluorotheylene, 1,1,1,-trifluoroethane, methyl fluoride, cyclopropane, other hydrocarbon gases, or any combination thereof. The mixtures can include any suitable mixture ratios including those based on chamber length, cell length, carrier gas composition, sample gas composition, and the like. In an embodiment, the sample gas in the closed chamber 106 can comprise a mixture of methane and ethane at a ratio of between about 4:1 and about 1:1. In another embodiment, the sample gas in the closed chamber 106 can comprise a mixture of methane and ethylene at a ratio of between about 6:1 and about 1:1. In yet another embodiment, the sample gas in the closed chamber 106 can comprise a mixture of methane and trifluoromethane at a ratio of between about 3:1 and about 1:3. In still another embodiment, the sample gas in the closed chamber 106 can comprise a mixture of methane having a concentration between about 20% and about 40% and ethane having a concentration between about 10% and about 30%, with the balance being an inert gas (e.g., a mixture of about 30% methane and about 18% ethane for use with a 40 mm light path 104). In some embodiments, the closed chamber 106 can comprise cyclopropane (e.g., 100% cyclopropane) for use in detecting one or more components of a solvent. In some embodiments, the sample gas in the closed chamber 106 can comprise a mixture of trifluoromethane and an inert gas.

Each of the sample gas mixture may be useful for determining a normalized response of flammable gases in the light path 104 relative to an LEL threshold. Various flammable gases can include, but are not limited to, ethanol, ethyl acetate, toluene, methyl ethyl ketone, isopropanol, acetone, n-hexane, n-heptane, cyclohexanon, butanol, o-xylene, p-xylene, methanol, dimethyl ether, benzene, butyl acetate, 1-methoxy-2-propanol, ethoxy propanol, methyl glycol, tetrahydrofuran, dimethylformamide, propyl acetate, methyl isobutyl ketone, methane, ethane, propane, butane, pentane, C6+ hydrocarbons, and any combination thereof.

In order to determine the concentration of the flammable gases relative to the applicable LEL threshold, the output of the photoacoustic sensor 100 can be determined over a range of gas concentrations for one or more flammable components using a mixture of gases as described above in the closed chamber 106. A correlation between the percentage of the LEL and the concentration of the flammable gas in the light path can be developed and used with the output acoustic signal from the acoustic sensor 108 to determine a flammability level relative to the LEL. The use of a plurality of sample gases in the closed chamber 106 to produce the normalized response over a broad range of flammable components in the light path represents an advantage relative to the need to determine each gas concentration individually and can be more accurate than past flammability detectors.

The use of a sample gas or a plurality of gases in the sample gas mixture within the closed chamber 106 has also been shown to be applicable to other normalized responses. For example, mixtures of sample gases can be used to determine an exposure level to various hydrocarbons, an exposure level relative to a toxicity threshold, or the like. As with the specific examples listed herein, a correlation between the sample gas mixture and the expected gases within the light path 104 (e.g., aromatic hydrocarbons, refrigerants, solvents, carbon monoxide, carbon dioxide, etc.) can be tested and measured, and the sample gas mixture can then be used with closed chamber 106 to provide a normalized response over a range of target gases within the light path 104.

In an embodiment, a sample gas or a plurality of gases can be used in the sample gas mixture within the closed chamber 106 to obtain a normalized response for a calorific value of a gas sample. The calorific value as used herein refers to the energy content of a fuel and represents a measurement of the amount of heat produced by the complete combustion of a specific quantity of the fuel. In this embodiment, mixtures of sample gases can be used to determine the calorific value of a gas (e.g., natural gas, etc.), for example, passing through a pipeline. Existing gas metering uses volumetric metering and customers can be billed for energy. However, the meter only tends to measure volume while the natural gas provider monitors and compensates for the varying aspects of the natural gas (pressure, temperature, and energy content), which can cause changes in the energy contained in a volume of the natural gas. As with the other examples listed herein, a correlation between the calorific value in various gas samples in the light path 104 and a sample gas mixture can be tested and measured, and the sample gas mixture can then be used with closed chamber 106 to provide a normalized response over a range of calorific values of a gas within the light path 104. Since it may be expected that a natural gas or other gas containing substantial amounts of hydrocarbons can absorb the radiation within the path length, the overall length of the light path 104 can be set to allow for the proper output signal strength in the closed cell.

In each of the normalized response determinations, the resulting normalized response can be compared to a threshold. For example, the normalized flammability limit can be output as a percentage of the LEL. The resulting output can be compared to a threshold percentage of the LEL, and an alarm or warning can be generated if the normalized response exceeds the threshold. This may allow for the monitoring of a condition that can be caused by a large range of gases, any one or more of which may be present at any given time. Thus, the photoacoustic sensor 100 with a plurality of sample gases may simplify the monitoring process for these types of conditions.

Figure 2:
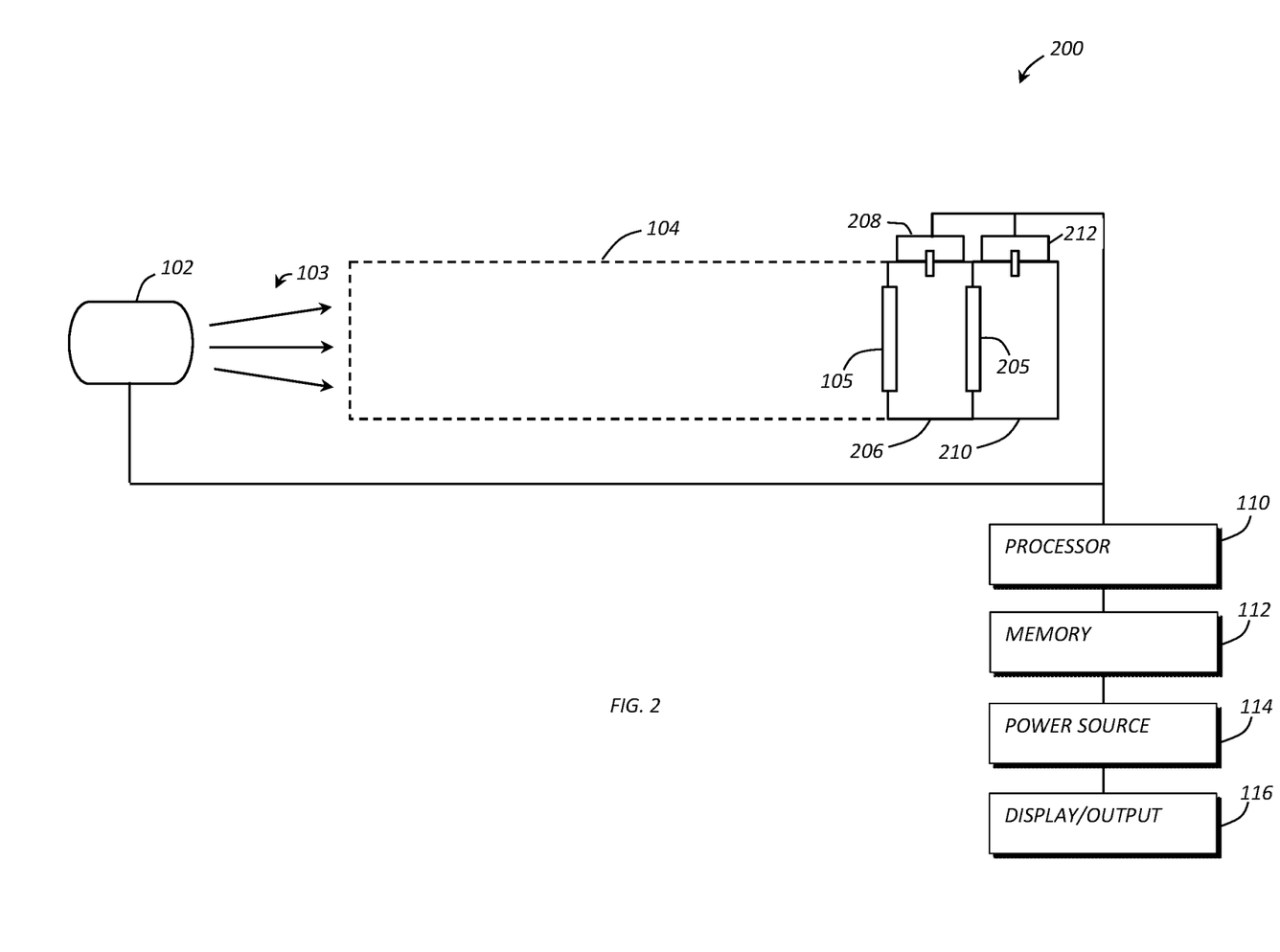
FIG. 2 schematically illustrates another photoacoustic sensor according to an embodiment.

Another embodiment of a photoacoustic sensor 200 is schematically illustrated in FIG. 2. The photoacoustic sensor 200 of FIG. 2 is similar in many aspects to the photoacoustic sensor 100 of FIG. 1, and similar components will not be discussed in detail in the interest of brevity. In general, the photoacoustic sensor 200 comprises a light source 102 producing radiation 103, a light path 104, a first closed chamber 206, a first acoustic sensor 208 in fluid communication with the interior of the first closed chamber 206, a second closed chamber 210, and a second acoustic sensor 212 in fluid communication with the interior of the second closed chamber 210. The light source 102, the light path 104, the processor 110, the memory 112, the power source 114, and the display device 116 can be the same or similar to the corresponding components described with respect to FIG. 1.

The main difference between the photoacoustic sensor 200 shown in FIG. 2 and the photoacoustic sensor 100 shown in FIG. 1 is the presence of a plurality of closed chambers 206, 210, each with an associated acoustic sensor 208, 212, respectively. Each closed chamber 206, 210 and the corresponding acoustic sensor 208, 212 may be the same or similar to the acoustic sensor and closed chamber described with respect to FIG. 1. In an embodiment, the closed chambers 206, 210 can be constructed of a transparent material as described above.

The multiple closed chambers 206, 210 can be arranged in a number of configurations. As shown in FIG. 2, the first closed chamber 206 may have a first window 105 disposed in a first wall. The first window 105 may allow the radiation that passes through the light path 104 to pass into the first closed chamber 206. A second window 205 can be disposed in a second wall of the first closed chamber 206, which may be a common wall between the first closed chamber 206 and the second closed chamber 210. The second window 205 may be sealingly engaged with the second wall to form a seal between the first closed chamber 206 and the second closed chamber 210. The housing forming the two closed chambers 206, 210 can be an integrated housing with an internal divider with the second window 205. The volumes and shapes of each closed chamber 206, 210 can be the same or different. In an embodiment, the second closed chamber 210 may have a different volume than the first closed chamber 206.

The first window 105 and the second window 205 can be formed from any of the materials described herein. In an embodiment, the first window 105 and the second window 205 are formed from the same material and may have approximately the same thickness. In order to allow the radiation to pass through the first closed chamber 206 and into the second closed chamber 210, the first window 105 and the second window 205 may be substantially aligned along a line extending towards the light source 102. In some embodiments, the first window 105, and the second window 205 can comprise different materials, and one or more optional filters can be associated with the first window 105 and/or the second window 205. For example, the second window 205 may filter the radiation 103, or alternatively have a separate filter for filtering the radiation 103, passing through the first closed chamber 206 to provide a different radiation spectrum for the radiation 103 passing into the second closed chamber 210.

In an embodiment, one or more of the first window 105 and/or the second window 205 can be formed as one or more lenses. For example, the first window 105 can be formed as a converging lens to gather and cause the radiation to converge into the first closed chamber 206. The second window 205 can comprise a converging or diverging lens. For example, the second window 205 may comprise a diverging lens to produce a shaped beam from the converging radiation passing through the first window 105. Any combination of shaped windows can be used to provide the desired light beam shape in the first closed chamber 206 and/or the second closed chamber 210.

In an embodiment, a mirrored surface can present in the first closed chamber 206 and/or the second closed chamber 210. In some embodiments, one or more of the windows 105, 205 can be replaced with a mirror or mirrored surface to reflect at least a portion of the radiation 103 back into the same closed chamber or other closed chambers. The mirrored surface may also, in some embodiments, reflect at least a portion of the radiation 103 back to the light source 102 or a reflective surface near the light source 102 as described in more detail above.

While shown as two closed chambers 206, 210 sharing a common window 205, the two closed chambers 206, 210 can also be separate closed chambers that are disposed adjacent to each other. In this embodiment, the first closed chamber 206 could comprise two windows opposite each other and aligned so that the light passing through the light path 104 can pass into the first closed chamber 206, through the interior and out of the closed cell on the opposite side. The second closed chamber 210 could comprise a window aligned with the two windows in the first closed chamber 206 so that radiation 103 passing through the first closed chamber 206 could pass into the second closed chamber 210. Any number of separate closed chambers with the appropriate alignment of the windows could be placed in series to allow the radiation to pass through the closed chambers in series.

The use of a plurality of closed chambers 206, 210 may provide for a number of different uses of the photoacoustic sensor 200. For example, the second closed chamber 210 can be used to hold a reference gas and/or the second closed chamber 210 can be used to hold a second sample gas for detecting different gases within the light path 104. In an embodiment, the first closed chamber 206 can retain a reference gas and the second closed chamber 210 can hold the sample gas.

In an embodiment, the second closed chamber 210 can be used to hold a reference gas. A reference gas can include a gas that absorbs a portion of the radiation 103 at a different frequency than the sample gas within the first closed chamber 206. In some embodiments, the reference gas may absorb radiation 103 at a different frequency than an expected gas within the light path 104. When the radiation 103 passes into the second closed chamber 210, the reference gas may produce an acoustic response that corresponds to the modulation frequency of the radiation 103. A suitable reference gas or mixture of reference gases may be selected based upon the sample gas or gasses present in the first closed chamber 206 as well as the expected gases present in the light path 104. In an embodiment, the reference gas can comprise nitrous oxide (e.g., NO2), diborane, combinations thereof, or any other gas or combination of gases that can produce an acoustic response at a frequency other than the gases of interest.

The use of a gas that may not be affected by the presence of any gases between the light source 102 and the second closed chamber 210 may provide a reference acoustic signal that can be detected by the second acoustic sensor 212. The reference signal may be used in several ways. First, the reference signal may provide an indication that radiation 103 is being produced by the light source 102. Without such an indication, the photoacoustic sensor 200 may provide a false indication as to the presence of a target gas.

The reference signal can also be used to provide a correction for the acoustic signal detected in the first closed chamber 206. The frequency range of the radiation 103 at which the reference gas absorbs may not be absorbed or otherwise filtered between the light source 102 and the second closed chamber 210. As a result, the reference gas may produce an acoustic response that is only affected by attenuation of the radiation 103 that is common to both the reference gas and the sample gas in the first closed chamber 206. For example, fogging of the first window 105 and/or the second window 205, a reduction in the output intensity of the light source 102, atmospheric attenuators such as dust, or the like may result in a decrease in the radiation intensity reaching the second closed chamber 210. Since these effects may be common to both the first closed chamber 206 and the second closed chamber 210, the reference signal can be used to compensate the detected signal from the first closed chamber 206 to produce a response with an improved accuracy.

In some embodiments, the plurality of closed chambers 206, 210 can both comprise sample gases. The sample gas in the first closed chamber 206 can be different than the sample gas in the second closed chamber 210. The ability to use two different samples that can each comprise one or more gases can allow for different target gases to be detected in the light path 104. In an embodiment, two different sample gases are retained in the two closed chambers 206, 210. When the absorption characteristics of the two sample gases do not overlap, or only overlap to a limited degree, a concentration value of a corresponding target gas in the light path 104 can be determined.

In an embodiment, when a target gas is present in the light path 104 that is the same as the first sample gas or that has similar absorption characteristics as the first sample gas, the reduction in the acoustic response in the first closed chamber 206 can be processed to determine a concentration value of the target gas in the light path. Similarly, when a second target gas is present in the light path 104 that is the same as the second sample gas or that has similar absorption characteristics as the second sample gas, the reduction in the acoustic response in the second closed chamber 206 can be processed to determine a concentration value of the second target gas in the light path 104. When both the first and second target gases are present in the light path at the same time, a reduction in the acoustic response in the first closed chamber 206 and the second closed chamber 210 can be used to determine a concentration value of first and second target gases at the same time. This may allow for individual concentration values of a plurality of target gases in the light path 104 to be determined simultaneously.

In some embodiments, a plurality of closed chambers 206, 210 can be used to provide one or more normalized responses along with a concentration value for a specific target gas. In this embodiment, one of the closed chambers 206, 210 may comprise a mixture of sample gases to provide a normalized response while another closed chamber can contain a sample gas to provide an individual concentration value of a target gas. The ability to combine multiple closed chambers 206, 210 in series can then be used to provide a variety of output responses according to the needs of the sensor.

While illustrated in FIG. 2 as having two closed chambers 206, 210, any number of closed chambers can be arranged in series. For example, 3, 4, 5, 6, or more closed chambers can be arranged in series to enable the detection of a concentration value of one or more components, one or more normalized responses, and/or the use of a reference signal to ensure the operation of the sensor and/or provide a correction signal.

While illustrated in FIG. 2 as being arranged in series, the plurality of closed chambers 206, 210 can also be arranged in parallel. For example, the cells can be stacked so that a single light source 102 can be incident on each cell of the plurality of closed chambers 206, 210 at the same time. The remaining components may be the same or similar. An arrangement in parallel can allow for sample gases that have overlapping absorption lines or ranges to be used for the simultaneous detection of one or more target gases. By arranging the closed chambers 206, 210 in parallel, the absorption of the radiation 103 by a sample gas in one of the closed chambers should not filter or prevent a sample gas in the second closed chamber 210 from being used to detect a signal over the absorption band. Further, in some embodiments, a plurality of closed chambers can be arranged in both parallel and series with multiple parallel rows of closed chambers having closed chambers also arranged in series.

Figure 3:
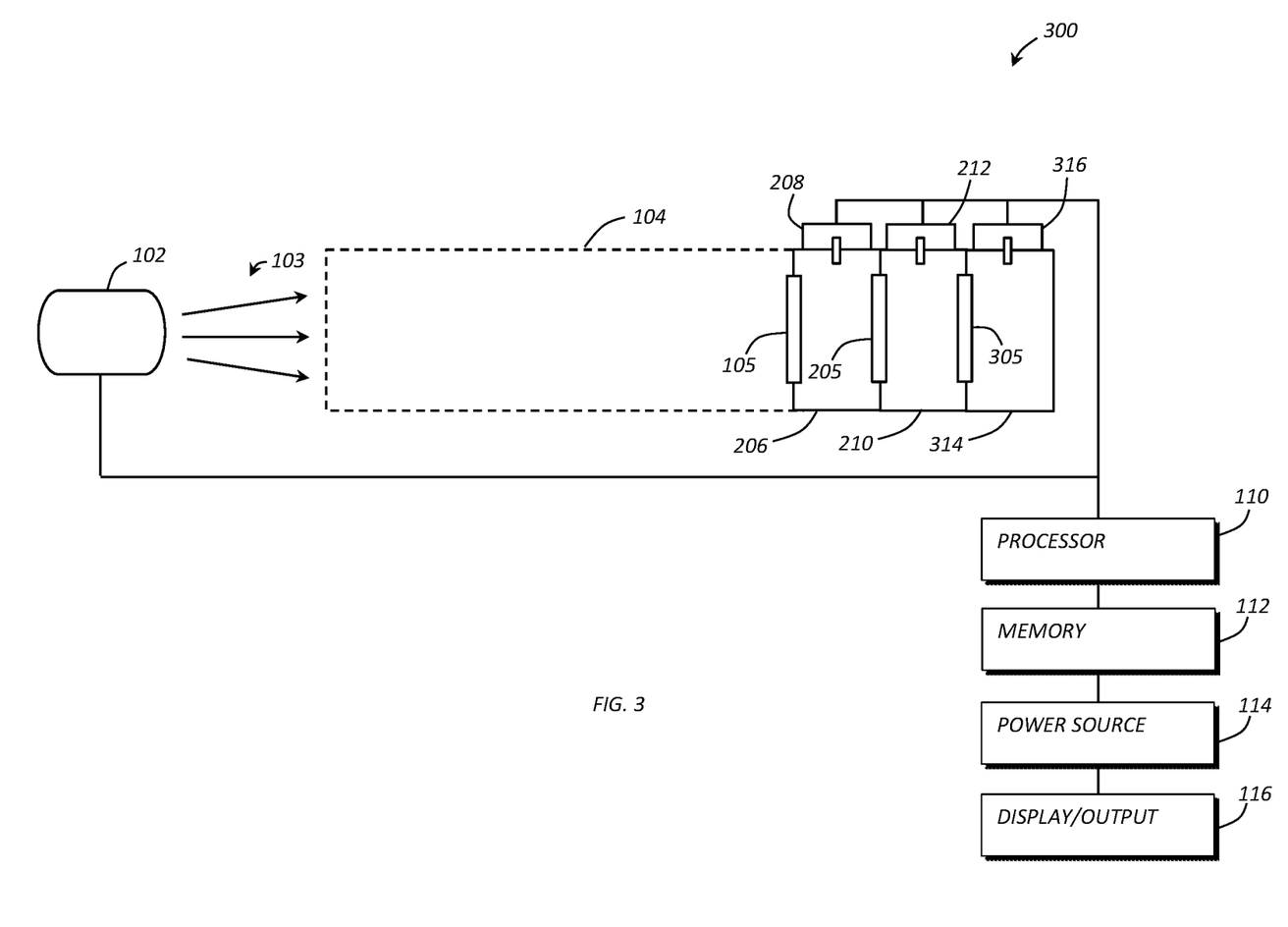
FIG. 3 schematically illustrates still another photoacoustic sensor according to an embodiment.

FIG. 3 schematically illustrates such an arrangement. In this embodiment, three closed chambers 206, 210, 314 can be arranged in series. This embodiment can be similar to the embodiment illustrated in FIG. 1 and FIG. 2, and similar elements will not be described in the interest of brevity. The main distinction between the photoacoustic sensor 300 of FIG. 3 and the previous photoacoustic sensors (e.g., sensor 100 and/or sensor 200) is the presence of the third closed chamber 314. As described herein, the three chambers can be formed with a single housing with windows 105, 205, 305 separating the closed chambers 206, 210, 314 and/or one or more of the closed chambers 206, 210, 314 can be a separate closed chamber arranged along the light path 104. One or more of the windows 105, 205, 305 can comprise a lens as described herein. The acoustic sensors 208, 212, 316 can be used to detect the acoustic response in the respective closed chambers 206, 210, 314.

In the embodiment shown in FIG. 3, the first closed chamber 206 and/or the second closed chamber 210 can be used in any of the ways described with respect to the two closed chambers illustrated in FIG. 2. The addition of the third closed chamber 314 may further allow for the use of a reference gas to provide a reference signal in addition to two concentration values for different target gases, two normalized response values using a mixture of sample gases, or a combination of a concentration value and a normalized response value. In some embodiments, the third closed chamber 314 could be used for a further concentration value determination or a normalized response value determination. The addition of one or more additional closed chambers could also provide additional responses.

Referring to FIG. 2 and FIG. 3, the photoacoustic sensors 200, 300 can be used to detect a gas in a light path 104. The detection process can occur by passing modulated radiation such as infrared radiation through a light path 104. In an embodiment, the radiation 103 can comprise a broad spectrum infrared radiation. The light path 104 can be open or enclosed, depending on the application. The light path 104 may comprise one or more target gases whose presence is being detected. When the one or more target gases are present, the target gases can absorb at least a portion of the infrared light in the light path 104. The remaining radiation 103 may comprise a spectrum having the intensity of the radiation 103 as the absorption lines decreased.

The infrared light can then be passed into a first closed chamber 206 through a first window 105. The window can be substantially transparent to infrared light, though an optional filter may be used to allow a selective range of frequencies or wavelengths to pass into the first closed chamber 206. The first closed chamber 206 can comprise a first sample of one or more gases. The interaction of the remaining radiation 103 with the first sample can generate an acoustic signal that can be detected by a first acoustic sensor 208. The acoustic signal can be generated in response to the absorption of a portion of the remaining radiation 103 by the sample gas in the first closed chamber 206. The resulting absorption may produce a temperature variation and corresponding pressure variation that corresponds to the modulation frequency of the radiation 103 passing through the light path 104.

The radiation 103 that is not absorbed in the light path 104 and the first closed chamber 206 can then pass out of the first closed chamber 206 and into a second closed chamber 210. The radiation 103 can pass through one or more windows between the first closed chamber 206 and the second closed chamber 210, where the window can be a common window that separates the two chambers from each other. The second closed chamber 210 can comprise one or more gases. The interaction of the remaining radiation 103 with the one or more gases in the second closed chamber 210 can generate a second acoustic signal that can be detected by a second acoustic sensor 212. The second acoustic signal can be generated in response to the absorption of a portion of the remaining radiation 103 by the one or more gases in the second closed chamber 210. The resulting absorption may produce a temperature variation and corresponding pressure variation that corresponds to the modulation frequency of the radiation 103 passing through the light path 104.

The outputs from the first acoustic sensor 208 and the second acoustic sensor 212 can pass to a processor 110. The processor 110 may use a correlation or comparison with a base level response when no target gases are present in the light path 104 to determine a reduction in the acoustic signals. The resulting reduction in the acoustic signals can be used to determine a response. Various corrections can be applied to the acoustic sensor outputs include corrections for pressure and temperature.

The response can comprise a concentration of a first target gas in the light path 104. When the first target gas is the same as one of the gases in the first closed chamber 206 or the second closed chamber 210, or has similar absorption characteristics to one of the gases in the first closed chamber 206 or the second closed chamber 210, the processor 110 can determine a concentration value for the target gas. The response can also include a concentration value for a second target gas in the light path 104. When the second target gas is the same as one of the gases in the first closed chamber 206 or the second closed chamber 210, or has similar absorption characteristics to one of the gases in the first closed chamber 206 or the second closed chamber 210, the processor 110 can determine a concentration value for the second target gas, which can occur at the same time as the determination of the concentration value for the first target gas.

In an embodiment, the one or more gases in the second closed chamber 210 can comprise a reference gas. The reference gas may have different absorption characteristics than the sample in the first closed chamber 206, and the reference gas may have different absorption characteristics than a gas expected to be present in the light path 104. As a result, the reference gas may produce an acoustic response that can be used to indicate interference from the materials in the window, a filter, or a reduction in the output of the light source producing the radiation. The response can then be corrected based on the acoustic output from the reference gas in the second closed chamber

EXAMPLES

The disclosure having been generally described, the following example is given as particular embodiments of the disclosure and to demonstrate the practice and advantages thereof. It is understood that the example is given by way of illustration and is not intended to limit the specification or the claims in any manner.

To demonstrate the use of the photoacoustic sensor as described herein, a filament bulb was used as a source with a 1000 nm wide filter in front to pass wavelengths in the ~3-4 micron range. The source/filter combination was placed approximately 40 mm away from the detector which was comprised of two stacked closed chambers. The "sample" closed chamber contained a mixture of methane (approx. 30% v/v) and ethane (approx. 18% v/v) with a balance of an inert gas such as nitrogen. The "reference" closed chamber contained (nitrous oxide) with an absorption cross section within the 3-4 micron wavelength band, but outside the absorption band for the hydrocarbons to be measured. The deviation of response with 4.4% Methane (50% LEL UK) contained within the path length (between the bulb and closed chambers) produced a measured deviation response of about 15% (against an $N_2$ baseline—no gas).

It is expected that other hydrocarbon gases will provide a similar deviation response. The results demonstrate the ability for a single calibration using a gas mixture that can provide a normalized response for a number of hydrocarbons.

Having described some systems and methods herein, various embodiments can include, but are not limited to:

In a first embodiment, a non-dispersive photoacoustic gas detector comprises: an infrared light source; a first closed chamber, wherein the first closed chamber comprises a plurality of windows that are substantially transparent to infrared light from the infrared light source; a second closed chamber, wherein the second closed chamber comprises at least one window that is substantially transparent to infrared light from the infrared light source, wherein the first closed chamber is arranged in series with the second closed chamber between the infrared light source and the second closed chamber; a first acoustic sensor in fluid communication with the first closed chamber; and a second acoustic sensor in fluid communication with the second closed chamber.

A second embodiment can include the non-dispersive photoacoustic gas detector of the first embodiment, wherein the first closed chamber comprises at least one sample gas.

A third embodiment can include the non-dispersive photoacoustic gas detector of the second embodiment, wherein the second closed chamber comprises at least one reference gas.

A fourth embodiment can include the non-dispersive photoacoustic gas detector of the third embodiment, wherein the at least one reference gas absorbs infrared light in a different portion of the infrared spectrum than the at least one sample gas.

A fifth embodiment can include the non-dispersive photoacoustic gas detector of any of the first to fourth embodiments, further comprising a light path disposed between the infrared light source and the first closed chamber.

A sixth embodiment can include the non-dispersive photoacoustic gas detector of the fifth embodiment, further comprising a sample chamber disposed between the infrared light source and the closed chamber, wherein the light path is disposed through the sample chamber.

A seventh embodiment can include the non-dispersive photoacoustic gas detector of the fifth or sixth embodiment, further comprising a processor in signal communication with the first acoustic sensor and the second acoustic sensor, wherein the processor is configured to convert a signal output from the first acoustic sensor and the second acoustic sensor into a concentration of at least one gas in the light path.

An eighth embodiment can include the non-dispersive photoacoustic gas detector of the seventh embodiment, wherein the at least one gas in the light path is the same as the at least one sample gas.

A ninth embodiment can include the non-dispersive photoacoustic gas detector of the seventh embodiment, wherein the at least one gas in the light path is different than the at least one reference gas.

A tenth embodiment can include the non-dispersive photoacoustic gas detector of any of the first to ninth embodiments, wherein the at least one window of the second closed chamber is one of the plurality of windows of the first closed chamber.

An eleventh embodiment can include the non-dispersive photoacoustic gas detector of any of the first to tenth embodiments, wherein at least one of the first closed chamber or the second closed chamber is formed from a transparent material.

A twelfth embodiment can include the non-dispersive photoacoustic gas detector of the eleventh embodiment, wherein the transparent material is substantially non-absorptive to infrared light from the infrared light source.

A thirteenth embodiment can include the non-dispersive photoacoustic gas detector of the eleventh or twelfth embodiment, wherein the transparent material comprises a glass.

A fourteenth embodiment can include the non-dispersive photoacoustic gas detector of any of the first to thirteenth embodiments, wherein at least one window of the plurality of windows of the first closed chamber is formed from a material, has a thickness, or both that is configured to filter at least a portion of the infrared light from the infrared light source.

In a fifteenth embodiment, a non-dispersive photoacoustic gas detector comprises: an infrared light source; a plurality of closed chambers arranged in series with respect to a light path from the infrared light source, wherein the plurality of closed chambers comprise a transparent pathway through the plurality of closed chambers; and a plurality of acoustic sensors, wherein each acoustic sensor of the plurality of acoustic sensors is associated with a corresponding closed chamber of the plurality of closed chambers, and wherein each acoustic sensor is in fluid communication with the corresponding closed chamber, wherein a first closed chamber of the plurality of closed chambers comprises a first sample gas, and wherein a second closed chamber of the plurality of closed chambers comprises a second sample gas, wherein the second sample gas has a different composition than the first sample gas.

A sixteenth embodiment can include the non-dispersive photoacoustic gas detector of the fifteenth embodiment, wherein a third closed chamber of the plurality of closed chambers comprises a reference gas, wherein the reference gas absorbs infrared light in a different wavelength range than the first sample gas or the second sample gas.

A seventeenth embodiment can include the non-dispersive photoacoustic gas detector of the fifteenth or sixteenth embodiment, further comprising a processor in signal communication with the plurality of acoustic sensors, wherein the processor is configured to convert a signal output from the plurality of acoustic sensors into a concentration of a plurality of gases in the light path.

An eighteenth embodiment can include the non-dispersive photoacoustic gas detector of the seventeenth embodiment, wherein at least one gas in the light path is the same as the first sample gas or the second sample gas.

A nineteenth embodiment can include the non-dispersive photoacoustic gas detector of the seventeenth or eighteenth embodiment, wherein a plurality of detectable gases are in the light path, wherein a first detectable gas of the plurality of detectable gases is the same as the first sample gas, wherein a second detectable gas of the plurality of detectable gases is the same as the second sample gas, and wherein the processor is configured to convert a plurality of output signals from the plurality of acoustic sensors into a concentration of the first detectable gas and a concentration of the second detectable gas.

A twentieth embodiment can include the non-dispersive photoacoustic gas detector of any of the fifteenth to twentieth embodiments, wherein the plurality of closed chambers comprises a plurality of windows, wherein at least one window of the plurality of windows is shared between at least two closed cells of the plurality of closed cells.

In a twenty first embodiment, a method of detecting a gas comprises: passing infrared light through a light path, wherein the light path comprises one or more target gases; absorbing, by the one or more target gases, at least a portion of the infrared light in the light path; passing the infrared light into a first closed chamber after passing the infrared light through the light path, wherein the first closed chamber comprises a plurality of windows that are substantially transparent to the infrared light, and wherein the first closed chamber comprises a first gas sample; generating a first acoustic signal within the first closed chamber in response to passing the infrared light into the first closed chamber; passing the infrared light through the first closed chamber into a second closed chamber, wherein the second closed chamber comprises at least one window that is substantially transparent to the infrared light; generating a second acoustic signal within the second closed chamber in response to passing the infrared light into the second closed chamber; detecting the first acoustic signal and the second acoustic signal; and converting the first acoustic signal and the second acoustic signal into a response.

A twenty second embodiment can include the method of the twenty first embodiment, wherein the response comprises a concentration of a first gas in the light path.

A twenty third embodiment can include the method of the twenty second embodiment, wherein the second closed chamber comprises a second gas sample, and wherein the responses comprise a concentration of a second gas in the light path.

A twenty fourth embodiment can include the method of any of the twenty first to twenty third embodiments, wherein the second closed chamber comprises a reference gas, and wherein the responses comprise a signal indicating the presence of the infrared light.

A twenty fifth embodiment can include the method of the twenty fourth embodiment, wherein the response further comprises an indication of the attenuation of the infrared light through the plurality of windows or the at least one window.

A twenty sixth embodiment can include the method of the twenty fifth embodiment, wherein the response further comprises an indication of the output power of the infrared light from an infrared light source.

A twenty seventh embodiment can include the method of the twenty fifth embodiment, wherein the reference gas is not present in the light path.

A twenty eighth embodiment can include the method of any of the twenty first to twenty seventh embodiments, wherein at least one of the first closed chamber or the second closed chamber is formed from a transparent material.

A twenty ninth embodiment can include the method of any of the twenty first to twenty eighth embodiments, further comprising: determining that the second acoustic signal is below a threshold; and generating an error signal indicating that a gas detector is not working.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A non-dispersive photoacoustic gas detector comprising:
   an infrared light source;
   a first closed chamber, wherein the first closed chamber comprises a plurality of windows that are substantially transparent to infrared light from the infrared light source;
   a second closed chamber, wherein the second closed chamber comprises at least one window that is substantially transparent to infrared light from the infrared light source,
   wherein the first closed chamber is arranged in series with the second closed chamber between the infrared light source and the second closed chamber, wherein the first closed chamber comprises at least one sample gas,
   wherein the second closed chamber comprises at least one reference gas, wherein the at least one reference gas comprises at least one of diborane or nitrous oxide or a combination thereof, and wherein the at least one reference gas absorbs infrared light in a different portion of the infrared spectrum than the at least one sample gas;
   a first acoustic sensor in fluid communication with the first closed chamber; and a second acoustic sensor in fluid communication with the second closed chamber.

2. The non-dispersive photoacoustic gas detector of claim 1, wherein the reference gas is configured to provide an indication of environmental effects on the acoustic response of the other closed chambers.

3. The non-dispersive photoacoustic gas detector of claim 1, further comprising a sample chamber disposed between the infrared light source and the first closed chamber, wherein the light path is disposed through the sample chamber.

4. The non-dispersive photoacoustic gas detector of claim 1, further comprising a processor in signal communication with the first acoustic sensor and the second acoustic sensor, wherein the processor is configured to convert a signal output from the first acoustic sensor and the second acoustic sensor into a concentration of at least one gas in the light path.

5. The non-dispersive photoacoustic gas detector of claim 4, wherein the at least one gas in the light path is the same as the at least one sample gas.

6. The non-dispersive photoacoustic gas detector of claim 1, wherein the at least one window of the second closed chamber is one of the plurality of windows of the first closed chamber.

7. The non-dispersive photoacoustic gas detector of claim 1, wherein at least one of the first closed chamber or the second closed chamber is formed from a transparent material.

8. The non-dispersive photoacoustic gas detector of claim 1, wherein at least one window of the plurality of windows of the first closed chamber is formed from a material, has a thickness, or both that is configured to filter at least a portion of the infrared light from the infrared light source.

9. A method of detecting a gas comprising:
passing infrared light through a light path, wherein the light path comprises one or more target gases;
absorbing, by the one or more target gases, at least a portion of the infrared fight in the light path;
passing the infrared light into a first closed chamber after passing the infrared light through the light path, wherein the first closed chamber comprises a plurality of windows that are substantially transparent to the infrared light, and wherein the first closed chamber comprises a first gas sample;
generating a first acoustic signal within the first closed chamber in response to passing the infrared fight into the first closed chamber, wherein the first closed chamber comprises at least one sample gas;
passing the infrared light through the closed chamber into a second closed chamber, wherein the second closed chamber comprises at least one window that is substantially transparent to the infrared light;
generating a second acoustic signal within the second closed chamber in response to passing the infrared light into the second closed chamber, wherein the second closed chamber comprises at least one reference gas, wherein the at least one reference gas is at least one of diborane or nitrous oxide or a combination thereof, and wherein the at least one reference gas absorbs infrared light in a different portion of the infrared spectrum than the at least one sample gas;
detecting the first acoustic signal and the second acoustic signal; and
converting the first acoustic signal and the second acoustic signal into a response.

10. method of claim 9, wherein the response comprises a concentration of a first
gas in the light path.

11. The method of claim 9, wherein the second acoustic signal generated by the at least one reference gas is configured to provide an indication or environmental effects on the acoustic response in the first closed chamber.

12. The method of claim 9, wherein the response comprises a signal indicating the presence of the infrared fight based on the second acoustic signal generated by the reference gas.

13. method of claim 12, wherein the response further comprises at least one of:
an indication the attenuation of the infrared light through the plurality of windows or the at least one window, or an indication of the output power of the infrared light from an infrared light source.

14. The method of claim 9, further comprising:
determining that the second acoustic signal is below a threshold; and
generating an error signal indicating detector is not working.

15. A non-dispersive photoacoustic gas detector comprising:
an infrared light source;
a plurality of closed chambers arranged in series with respect to a light path from the infrared light source, wherein the plurality of closed chambers comprise a transparent pathway through the plurality of closed chambers; and
a plurality of acoustic sensors, wherein each acoustic sensor of the plurality of acoustic sensors is associated with a corresponding closed chamber of the plurality of closed chambers, and wherein each acoustic sensor is in fluid communication with the corresponding closed chamber,
wherein a first closed chamber of the plurality of closed chambers comprises a first sample gas, and wherein a second closed chamber of the plurality of closed chambers comprises a reference gas, wherein the reference gas comprises at least one of diborane or nitrous oxide or at least a combination thereof, wherein the reference gas absorbs infrared light in a different wavelength range than the first sample gas or the second sample gas.

16. The non-dispersive photoacoustic gas detector of claim 15, wherein a third closed chamber of the plurality of closed chambers comprises a second sample gas, wherein the second sample gas has a different composition than the first sample gas.

17. The non-dispersive photoacoustic gas detector of claim 15, further comprising a processor in signal communication with the plurality of acoustic sensors, wherein the processor is configured to convert a signal output from the plurality of acoustic sensors into a concentration of a plurality of gases in the light path.

18. The non-dispersive photoacoustic gas detector of claim 16, wherein at least one gas in the light path is the same as the first sample gas or the second sample gas.

19. The non-dispersive photoacoustic gas detector of claim 16, wherein a plurality of detectable gases are in the light path, wherein a first detectable gas of the plurality of detectable gases is the same as the first sample gas, wherein a second detectable gas of the plurality of detectable gases is the same as the second sample gas, and wherein the processor configured to convert a plurality of output signals from the plurality of acoustic sensors into a concentration of the first detectable gas and a concentration of the second detectable gas.

\* \* \* \* \*